United States Patent
Lin et al.

(10) Patent No.: US 7,959,684 B2
(45) Date of Patent: Jun. 14, 2011

(54) METHOD FOR FORMING A BIORESORBABLE COMPOSITE IMPLANT IN A BONE

(75) Inventors: Jiin-Huey Chern Lin, Winnetka, IL (US); Chien-Ping Ju, Carbondale, IL (US); Pong-Jeu Lu, Tainan (TW)

(73) Assignee: Joy Medical Devices Corporation, Kaohsiung (TW)

( * ) Notice: Subject to any disclaimer, the term of this patent is extended or adjusted under 35 U.S.C. 154(b) by 232 days.

(21) Appl. No.: 12/230,828

(22) Filed: Sep. 5, 2008

(65) Prior Publication Data

US 2009/0069900 A1    Mar. 12, 2009

Related U.S. Application Data

(60) Provisional application No. 60/993,203, filed on Sep. 11, 2007.

(51) Int. Cl.
*A61F 2/28* (2006.01)

(52) U.S. Cl. ............... 623/23.62; 623/23.51; 623/23.61

(58) Field of Classification Search ............... 623/23.48, 623/23.51, 23.61–23.62; 606/92–94
See application file for complete search history.

(56) References Cited

U.S. PATENT DOCUMENTS

| | | | |
|---|---|---|---|
| 6,726,691 B2 * | 4/2004 | Osorio et al. | 606/94 |
| 2003/0028251 A1 * | 2/2003 | Mathews | 623/17.16 |
| 2004/0186481 A1 * | 9/2004 | Chern Lin et al. | 606/92 |
| 2004/0230309 A1 * | 11/2004 | DiMauro et al. | 623/17.12 |
| 2005/0209629 A1 * | 9/2005 | Kerr et al. | 606/192 |
| 2006/0121084 A1 * | 6/2006 | Borden et al. | 424/426 |
| 2007/0185231 A1 * | 8/2007 | Liu et al. | 523/116 |

FOREIGN PATENT DOCUMENTS

WO    WO2006/138398    * 12/2006

* cited by examiner

*Primary Examiner* — Corrine M McDermott
*Assistant Examiner* — Rebecca Straszheim
(74) *Attorney, Agent, or Firm* — Bacon & Thomas, PLLC

(57) ABSTRACT

A method for forming a composite implant in a bone cavity is disclosed, which includes i) forming a first bone filler in a bone cavity; and ii) inserting a second bone filler into an unfilled space in the bone cavity, wherein the first bone filler has a higher compressive strength and slower bioresorption rate in comparison with the second bone filler.

22 Claims, 1 Drawing Sheet

METHOD FOR FORMING A BIORESORBABLE COMPOSITE IMPLANT IN A BONE

CROSS-REFERENCE TO RELATED APPLICATION

This patent application claims the benefit under 35 USC 119(e) of U.S. Provisional Patent Application No. 60/993,203, filed Sep. 7, 2007.

FIELD OF THE INVENTION

The present invention is related to a technique for forming a bioresorbable composite implant in a bone cavity, and in particular to a method comprising forming a hardened orthopaedic paste in a bone cavity under pressure and with a leaking mechanism so that the compressive strength thereof is increased, and inserting another bone filler into an unfilled space in the bone cavity, which has a higher bioresorption rate in comparison with the hardened orthopaedic paste.

BACKGROUND OF THE INVENTION

It is well accepted that bioresorbable orthopedic implants are always the better choice than permanent foreign-body implants, as long as their bioresorption rates, biomechanical properties and variations in biomechanical properties with respect to the resorption processes are appropriately controlled. Among all bioresorbable orthopedic implants, calcium-based implants (calcium phosphate, calcium sulfate, etc), are perhaps the top choice so far.

For the purpose of filling a bone cavity, especially an irregularly-shaped bone cavity, a bone cement paste (for example, a PMMA, calcium phosphate cement or calcium sulfate cement) is often injected into the cavity, wherein the bone cement paste is hardened in-situ. This hardened cement will remain in bone as a permanent implant if it is a permanent foreign-body implant such as PMMA, or gradually replaced by natural bone if it is a bioresorbable material such as calcium phosphate or calcium sulfate. For load-bearing applications, this hardened cement should provide a sufficient strength to withstand the post-operation routine loadings.

Most conventional methods of forming a hardened (set) bone cement in bone cavity involve creating a bone cavity, followed by directly injecting a cement paste into the bone cavity. Such an approach suffers the following major drawbacks among others:

(1) Since the cement paste is directly injected into an environment filled with blood/body fluid, the cement particles are easily dispersed in this environment, especially before the paste is fully set. The dispersed cement particles can penetrate into surrounding tissues, cracks, blood vessels, nerve system, etc. and cause various kinds of clinical complications such as potentially fatal cement embolism.

(2) Since the cement paste is hardened in blood/body fluid, the predetermined liquid/powder ratio, which is critical to cement properties, is disrupted in-situ, causing the performance/properties of the cement to degrade. Although applying pressure to the cement during its hardening process can improve the cement strength, surgeons usually avoid applying a high pressure directly to the injected cement paste due to the above-mentioned potential risks of complications.

(3) Besides the disruption in liquid/powder ratio, the irregular shape of the hardened cement also decreases the biomechanical properties of the cement and increases the uncertainty/risks of the cement performance (depending on the actual shape and filling condition), especially for bioceramic cements such as calcium phosphate cement and calcium sulfate cement. The decreased strength further causes the cement to more easily disperse/disintegrate.

Another approach to inject an orthopedic implant into a bone cavity involves inserting a container (balloon or pocket) into the cavity; injecting a bone filler (not necessarily a hardenable cement paste) into the container through a tube; and separating the container from the tube with the container and its contained bone filler remaining in bone. One major problem with this approach is that the container left in bone becomes a permanent foreign body which prevents the bone filler from directly interacting with bone tissue to form a biological or even only a chemical or physical bond between the bone filler and bone. Furthermore, most popularly-used containers (balloons) are made from polymers which are not bioactive, bioconductive, or even biocompatible. The negative effects of this permanently implanted container are most obvious when the bone filler is a bioresorbable material, such as a calcium phosphate or calcium sulfate-based material. In this case even a biodegradable polymer container hinders the bioresorption process of the bioresorbable bone filler for a season, especially during the most critical early stage resorption/healing process. Furthermore, most biodegradable polymers do not demonstrate mechanical properties as desired.

An improved method for forming a hardened cement in a bone cavity involves inserting an inflatable, preferably inflatable and expandable, pocket into a bone being treated; injecting a hardenable cement paste into the pocket through a tube which connects and carries the pocket into the bone; allowing the cement paste to harden within the pocket in the bone cavity; opening the pocket; separating the pocket from the hardened cement, and retrieving the opened pocket from the bone with the hardened cement remaining in the bone. Advantages of this method include allowing the hardened cement implant to directly contact the surrounding bone tissue thus enhancing the healing process, and the much higher strength of the hardened cement compared to that of the cement paste directly injected into the bone cavity. This is especially advantageous for bioresorbable implants. A typical example can be found in U.S. Pat. No. 7,306,610 B2.

A further improved method for forming a hardened cement in a bone cavity involves inserting an inflatable, preferably inflatable and expandable, pocket into a bone being treated; injecting a hardenable cement paste into the pocket through a tube which connects and carries the pocket into the bone, therein said pocket is made from a material penetrable to liquid but substantially impenetrable to the powder of said cement paste; allowing the cement paste to harden within the pocket in the bone cavity; opening the pocket; separating the pocket from the hardened cement, and retrieving the opened pocket from the bone with the hardened cement remaining in the bone. A primary advantage of this method is allowing a portion of the liquid contained in the cement paste to be expelled out of the pocket, especially when a pressure is applied unto said cement paste before said cement paste is substantially hardened, so that the powder/liquid ratio of said cement paste in said pocket is increased and the strength of the hardened cement is further increased. This further increase in cement strength is especially advantageous for the relatively weak ceramic, calcium-based cement. Typical examples can be found in U.S. Pat. No. 7,144,398 B2, WO 2004/093733, and WO 2006/138398.

Nevertheless, one disadvantage for the prior art pocket-injection approach is that there exists a portion of the bone cavity which cannot be filled due to the generally irregular shape of the cavity. Although the hardened cement implant may be strong enough to support the restored/expanded bone structure, the remaining (unfilled) cavity can act as a weak spot to potentially induce subsequent local fracturing. Such unfilled space can also induce the undesirable fibrous tissue ingrowth. Another potential problem is that, once the implant resorption process becomes significant, the new bone-incorporated cement implant may become too weak to support the structure. This can potentially cause subsequent fracture/collapse, if the resorption rate of the hardened cement is not carefully controlled.

SUMMARY OF THE INVENTION

The present invention discloses a method for forming a bioresorbable composite implant in a bone cavity, which overcomes most aforementioned difficulties/problems. The primary improvement step of the present invention is inserting a second bone filler with different resorption rate, structure and/or properties into the remaining (unfilled) cavity after the first bone filler (a cement paste) is hardened in a cavity in the bone being treated, wherein the hardened first bone filler and the second bone filler forming a composite implant in the bone cavity.

A method for forming a composite implant in a bone cavity disclosed in the present invention comprises i) forming a first bone filler in a bone cavity; and ii) inserting a second bone filler into an unfilled space in said bone cavity, wherein the first bone filler has a higher compressive strength and slower bioresorption rate in comparison with the second bone filler.

Preferably, the first bone filler comprises a hardened first orthopaedic paste as a major portion thereof, and the second bone filler comprises a hardened second orthopaedic paste as a major portion thereof, wherein the hardened first orthopaedic paste and the hardened second orthopaedic paste are both bioresorbable materials, and the hardened second orthopaedic paste has a porosity 20% higher than that of the hardened first orthopaedic paste. More preferably, the hardened second orthopaedic paste has a porosity 40% higher than that of the hardened first orthopaedic paste.

Preferably, said inserting in step ii) comprises injecting the second orthopaedic paste into the unfilled space in said bone cavity, and letting the second orthopaedic paste harden in the unfilled space.

Preferably, said inserting in step ii) comprises inserting a tube into the unfilled space in said bone cavity through a minimally invasively percutaneous path; injecting the second orthopaedic paste into the unfilled space in said bone cavity through said tube; letting the second orthopaedic paste harden in the unfilled space; and removing said tube from said percutaneous path.

Preferably, the second bone filler is in granular form.

Preferably, the second orthopaedic paste is calcium phosphate cement paste, calcium sulfate cement paste, or bioactive glass-based cement paste. More preferably, the second orthopaedic paste is further doped with a bone morphogenic protein (BMP), a growth factor, or living cells for enhancing bone resorption/healing processes, or the second orthopaedic paste is further doped with calcium phosphate particles, calcium sulfate particles, or bioactive glass particles.

Preferably, the first orthopaedic paste is calcium phosphate cement paste, calcium sulfate cement paste, or bioactive glass-based cement paste. More preferably, the first orthopaedic paste is further doped with calcium phosphate particles, calcium sulfate particles, or bioactive glass particles for improving the compressive strength.

Preferably, the first bone filler and the second bone fillers are both bioresorbable materials, and the second bone filler has a bioresorption rate higher than the first bone filler by at least 50%.

Preferably, said forming in step i) comprises inserting a major portion of a perforated balloon in said bone cavity; injecting the first orthopaedic paste into said perforated balloon, wherein said perforated balloon comprises a neck adapted to be mounted on an end of a tube through which said first orthopaedic paste is injected into the perforated balloon, and leaking perforations, wherein said leaking perforations have a size which is penetrable to liquid contained in said first orthopaedic paste but substantially impenetrable to powder contained in said orthopaedic paste under an expanded condition of said perforated balloon; letting the first orthopaedic paste harden in the perforated balloon under pressure, wherein said liquid contained in said first orthopaedic paste escapes from said perforated balloon through said perforation during said injection and hardening of said first orthopaedic paste; opening the perforated balloon when the first orthopaedic paste hardens or partially hardens; and retrieving the opened balloon from the bone cavity by pulling said tube to leave the hardened or partially hardened orthopaedic paste in the bone cavity.

Preferably, said opening comprises continuously or intermittently injecting a liquid or gas into the perforated balloon containing the hardened or partially hardened first orthopaedic paste therein until the perforated balloon is dilated to exceed a critical size, and thus ruptures.

Preferably, a rupture array is formed on said perforated balloon for initiating said rupture of said perforated balloon when the perforated balloon is dilated to exceed said critical size.

Preferably, a forced-feeding mechanism having a liquid or gas reservoir is connected to another end of the tube, and said liquid or gas is continuously or intermittently injected from the reservoir into the perforated balloon through said tube by applying a force to said forced-feeding mechanism, until the perforated-balloon is dilated to exceed said critical size. More preferably, said forced-feeding mechanism is a syringe.

Preferably, said rupture array comprises pores, dents, notches, grooves or cuts formed on said perforated balloon, which function as weak spots so that said rupture occurs along at least a portion of said weak spots. More preferably, said weak spots form one or more dotted lines.

Preferably, said rupture array is located in a region opposite to said neck of said perforated balloon.

Preferably, said weak spots form one dotted line across an apex of the perforated balloon or more dotted lines intersect at an apex of the perforated balloon.

Preferably, said rupture array comprises pores having a size which is penetrable to liquid contained in said orthopaedic paste but substantially impenetrable to powder contained in said orthopaedic paste under an expanded condition of said perforated balloon. More preferably, said pores constitutes a portion of said leaking perforations. Alternatively, said pores constitutes whole said leaking perforations.

DETAILED DESCRIPTION OF THE INVENTION

Figure 1:
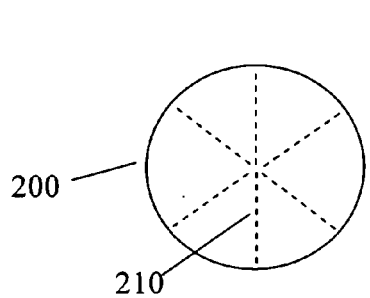
FIG. 1 is a schematic front view of a perforated balloon for entrapping an orthopaedic paste in a bone cavity until the paste is hardened in a bone cavity disclosed in WO 2006/138398.

The present invention discloses a method for forming a composite implant in a bone cavity comprising (a) preparing a first bone filler comprising a cement paste; (b) inserting a pocket into said bone; (c) injecting said first bone filler into said pocket, wherein said injecting is carried out with a means which is able to be operated outside said bone cavity; (d) allowing said cement paste at least partially harden in said pocket, wherein said cement paste in said pocket is optionally under a pressure while said cement paste is hardening in said pocket; (e) opening said pocket, wherein said opening is carried out with a means which is able to be operated outside said bone cavity, and the resulting opened pocket is attached to said means; (f) separating the resulting opened pocket from said hardened cement, wherein said separating is carried out by removing the resulting opened pocket from said bone cavity with the hardened cement remaining in said bone cavity; (g) inserting a second bone filler into said cavity, wherein the hardened first bone filler and the second bone filler forming a composite implant in said bone cavity.

The method of the present invention further comprises preparing a minimally invasively percutaneous path for the pocket to be inserted into the bone being treated.

The method of the present invention further comprises inserting an injection tube into the bone through said percutaneous path, therein the pocket is connected to or near distal end of said injection tube.

The pocket used in the method of the present invention is preferably made from a material penetrable to liquid but substantially impenetrable to the powder of said cement paste under expanded condition.

The pocket used in the method of the present invention preferably comprises at least one perforation through the membrane of said pocket, therein the perforation size can be controlled so that the pocket is penetrable to liquid but substantially impenetrable to the powder of said cement paste under expanded condition.

Step (d) of the method of the present invention preferably further comprises applying a pressure unto said cement paste before said cement paste is substantially hardened, causing a portion of the liquid contained in said cement paste to be expelled out of the pocket, so that the powder/liquid ratio of said cement paste in said pocket is increased.

The pocket used in the method of the present invention preferably comprises a designed pattern (perforation size, number and distribution) of perforations through the membrane of said pocket; therein a first portion of said perforations are able to function as channels through which said a portion of the liquid contained in said cement paste can be expelled out of the pocket; therein a second portion of said perforations are able to function as "weak spots" wherein said opening in (e) can preferentially occur at (along) said weak spots; wherein said first portion of said perforations and second portion of said perforations are optionally the same perforations.

Step (e) of the method of the present invention preferably comprises opening the pocket by means of a cutting mechanism, a thermal softening/melting mechanism, or a "forced-feeding" mechanism; wherein said cutting is conducted unto at least a portion of said pocket with a cutting means, for example, a thin wire or blade; said thermal softening/melting is conducted with an energy directed by an electrically, thermally or optically conductive wire embedded in at least a portion of said pocket; said "forced-feeding" is characterized by, after said cement paste is substantially hardened, further injecting a biocompatible fluid (water, oil, etc) into the pocket at a flow rate greater than that of the fluid leaking out of the pocket to cause said pocket to swell until it ruptures.

The method of the present invention further comprises, prior to inserting a pocket into the bone, creating a cavity and/or restoring at least a portion of height of the bone being treated, wherein the volume of the first bone filler injected into the pocket can be controlled to either avoid further expanding the bone, or to further expand the bone.

At least one of said first bone filler and second bone filler is a synthetic bioresorbable material. Preferably said first bone filler and said second bone filler are both bioresorbable materials. More preferably the second bone filler has a higher bioresorption rate than the first bone filler. Most preferably the second bone filler has a bioresorption rate higher than the first bone filler by at least 50%.

The second bone filler further has a more porous structure than the first bone filler. Preferably the second bone filler has a porosity volume fraction greater than the first bone filler by at least 20%; more preferably by at least 40%.

The first bone filler further has a higher compressive strength than the second bone filler.

The first bone filler material is preferably a viscous, flowable and hardenable calcium-based paste material, e.g., calcium phosphate-based or calcium sulfate-based cement paste; said first bone filler material is optionally doped with a relatively strong and rigid biocompatible phase, such as dense calcium phosphate particles, calcium sulfate particles, or bioactive glass particles, for improving strength.

The second bone filler material can be in granular form, cement paste form, or a granule-cement composite form; said second bone filler is preferably a calcium phosphate, calcium sulfate, or bioactive glass-based material; said second bone filler material preferably has a porous structure with a porosity volume fraction greater than about 50%, preferably greater than 70%; said second bone filler material is optionally doped with a BMP, a growth factor (e.g., a bone marrow or blood-derived growth factor), or living cells for enhancing bone resorption/healing processes.

The second bone filler can be delivered into the unfilled bone cavity through the same percutaneous path or a different percutaneous path.

The bone being treated is preferably a diseased or fractured vertebral body.

When the second bone filler of said composite implant is in granular form, the maximum dimension of the granules is preferably less than 3 mm, more preferably less than 2 mm, most preferably less than 1 mm, capable of being delivered through a minimally invasive percutaneous path or tube.

The bone being treated is preferably a diseased or fractured vertebral body.

Major advantages of this composite bone filler design are listed as follows:

Both first bone filler and second bone filler are bioresorbable materials and eventually the entire composite implant will be entirely replaced by natural bone.

The relatively strong first bone filler hardened from a cement paste within a pocket under pressure functions as a primary load-bearer and supports the treated/restored bone structure against collapse or subsequent fracture, while the second bioresorbable bone filler provides a fast bioresorption/healing process for the wounds.

The relatively low bioresorption rate of the first bone filler allows the resorption/healing processes associated with the fast-resorbable second bone filler to be substantially completed before the first bone filler starts to be significantly resorbed which may cause the first bone filler to become too weak to support the structure during its resorption process. (Cracks may occur accompanying the resorption process of a bioresorbable implant and thus weaken the implant structure) In the present composite implant design, at the time the first bone filler starts to be significantly resorbed, the second bone filler will have readily been replaced by natural bone which will help bear loads.

Figure 2:
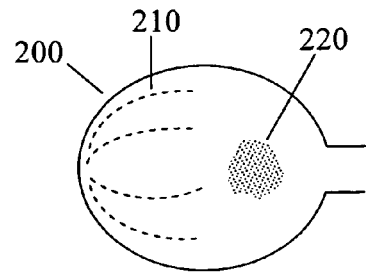
FIG. 2 is a schematic side view of the perforated balloon shown in FIG. 1.

In order for the balloon to be ruptured in a predetermined (designed) manner (pattern) after the cement is hardened, "perforation array" is designed, for example the perforation array 210 shown in FIGS. 1 and 2. The perforation array 210 is used mainly to rupture the inflated balloon 200 with predetermined lines/pattern of breakup, although permeability effect is also provided therein when the pore size is carefully controlled. The perforation array is also designed to keep the entire ruptured balloon to remain attached to the injection tube end after being ruptured. Without this design, it is highly likely that some random pieces of the ruptured balloon are detached from the balloon and left permanently in the bone cavity. Ideally the entire balloon should remain attached to the injection tube after being ruptured and can be entirely withdrawn along with the tube.

The perforation array 210 comprises designed patterns of pores, dents, notches, grooves, cuts, etc. and are made on the surface of at least a portion of the balloon. Such pores, dents, notches, grooves, cuts, etc. can be made by any conventional methods. Preferably, these pores, dents, notches, grooves, cuts, etc. are made at or near the central part of the balloon. Preferably, the "lines of perforation" converge around the apex of the balloon, creating relatively weakened spots where rupturing crack would initiate.

Such parameters as pore size, population, spacing between perforations, number of perforation array, and the array size are to be controlled and optimized to result in a required structural characteristics of the balloon.

Although permeability (draining) effect is provided in the design of the perforation array, in order to more effectively drain water and air out of the balloon as the cement paste is injected to fill the bone cavity, micro-pores 220 can be further incorporated over the surface of the balloon 200. These micro-pores can be distributed randomly or in a designed manner/pattern and will be progressively enlarged as cement mixture is continually delivered into the balloon.

The perforations of the perforation array 210 and the micro-pores 220 of desired diameters and optionally desired distribution (pattern) can be made mechanically (for example, by needle drilling), chemically (for example, by etching/dissolving) or thermally (for example, by focused heat or laser drilling). The perforations/pores can be made on an empty balloon, a balloon still attached onto a substrate mode (for example, a balloon made by dipping a balloon-shaped substrate mode of a desired size and shape in a PU solution), or a pre-expanded balloon with an infilling material.

As perforations/pores are made on a pre-expanded balloon, the infilling material can be any material which can be delivered into and expand the balloon, and removed from the balloon after perforations are made on the expanded balloon. The infilling material is preferably a high-viscosity powder-liquid mixture paste which will not set/harden in a short period of time after mixing (for example, a CaO powder/water mixture). The balloon can be pre-expanded to any desired size whereas perforations are made. One advantage for perforations/pores made on a pre-expanded balloon is its easier control in perforation quality, since the balloon surface is enlarged during expansion.

As a balloon swells to certain critical size, the internal stresses developed in the stretched membrane will reach the balloon fracture stress threshold. The corresponding strain at balloon fracture can be converted into the rupture volume of the balloon. When balloon is filled with any material which expands the balloon to this critical volume, balloon will fracture spontaneously and the fractured balloon membrane will shrink to its zero-stress state size. Balloon extraction can hence be achieved while leaving the solidified cement deployed in the designated bone cavity.

Figure 3:
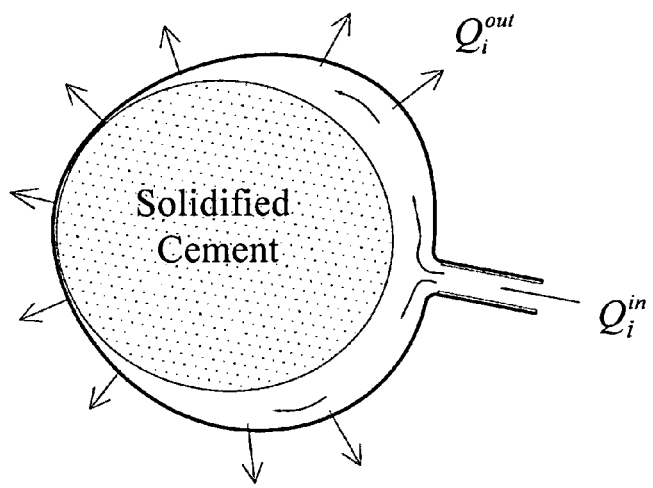
FIG. 3 is a schematic side view of a cement-filled balloon under forced-feeding by fluid.

FIG. 3 shows a cement-filled balloon under forced-feeding by fluid. As the feeding pressure destroys the initial static equilibrium the solidified cement will be lifted up immediately with an inlet flow passage created around the feeding entrance, followed by a filling of the balloon due to the infused fluid volume. Any fluid, gas or liquid, can be used as the filling material so long as it is biocompatible. These fluid fillers first separate the balloon membrane from the solidified cement surface, greatly reducing the contact friction by generating a layer of fluid buffer. Then a further injection of fluid filler will expand the balloon until balloon rupture is accomplished. According to the mass conservation of fluids, the rate of mass increment contained in the balloon closure is equal to the net mass flux convected through the inflow/outflow tracts:

$$\rho \frac{dV}{dt} = \sum_i \rho Q_i^{in} - \sum_i \rho Q_i^{out} \qquad (2)$$

in which, V is the volume and ρ is the density of the fluid while $Q_i^{in}$ and $Q_i^{out}$ are the inflow and outflow volume flowrates, respectively. For the case illustrated in FIG. 3, $Q_i^{in}$ is the forced-feeding influx and $$\sum_i Q_i^{out}$$

is the net outflux contributed by all the leakage flows across the micro-pores and perforations in the membrane wall. So long as the volume flux of the inflow is greater than that of the outflow, the balloon will keep on swelling until it ruptures.

Figure 4:
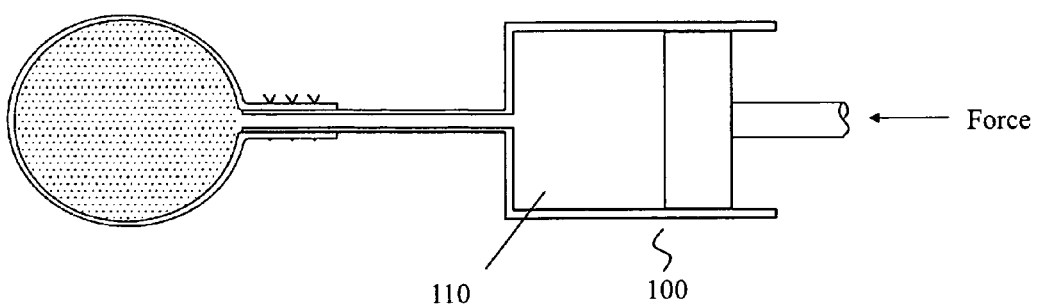
FIG. 4 is a schematic side view showing a representative implementation of forced-feeding by connecting the balloon rear end to a syringe.

FIG. 4 shows a representative implementation by connecting the balloon rear end to a fluid filler such as a syringe 100 having a fluid reservoir 110. Any decrease of the reservoir volume by pushing the syringe 100 from behind, with sufficiently force and speed, may result in a net volume infusion into the balloon. Balloon will rupture as the accumulated fluid mass increases and the resultant membrane stresses reach the rupture threshold value.

To reduce the risk that a portion (especially the leading/top portion) of ruptured balloon (especially for rupture occurring around the belly/equator portion of the balloon) being trapped in the cavity when the ruptured balloon is retrieved from the cavity site, a thread can be connected to any part of the balloon as a safety device. Since the leading/top portion is one that most easily breaks off the balloon during rupture, the thread can be connected (for example, by glue) to such location. In case a portion of ruptured balloon is broken off, the broken-off piece can be retrieved by the connected wire/thread independently.

A second bone filler is now delivered into the unfilled bone cavity with an injection tube through the same percutaneous path after the ruptured balloon being withdrawn from the bone cavity. The second bone filler is preferably a high-viscosity powder-liquid mixture paste the same as the hardened cement already in the bone cavity, or optionally doped with additional BMP, a growth factor, or living cells for enhancing bone resorption/healing processes. Preferably, the injection tube is kept in the percutaneous path and the injection pressure is maintained for a period of time so that the injected paste hardens or partially hardens in the unfilled bone cavity. The injection tube is then removed from the percutaneous path to complete the implantation of a composite filler in the bone cavity.

The invention claimed is:

1. A method for forming a composite implant in a bone cavity comprising i) forming a first bone filler in a bone cavity; and ii) inserting a second bone filler into an unfilled space in said bone cavity, wherein the first bone filler has a higher compressive strength and slower bioresorption rate in comparison with the second bone filler
wherein said forming in step i) comprises
inserting a major portion of a perforated balloon in said bone cavity;
injecting the first bone filler comprising a first orthopaedic paste into said perforated balloon, wherein said perforated balloon comprises a neck adapted to be mounted on an end of a tube through which said first bone filler is injected into the perforated balloon; and leaking perforations, wherein said leaking perforations have a size which is penetrable to liquid contained in said first orthopaedic paste but substantially impenetrable to powder contained in said orthopaedic paste under an expanded condition of said perforated balloon;
letting the first orthopaedic paste harden in the perforated balloon under pressure, wherein said liquid contained in said first orthopaedic paste escapes from said perforated balloon through said perforations during said injection and hardening of said first orthopaedic paste;
opening the perforated balloon when the first orthopaedic paste hardens or partially hardens; and
retrieving the opened balloon from the bone cavity by pulling a tube on which said neck is mounted to leave the hardened or partially hardened orthopaedic paste in the bone cavity,
wherein said opening comprises continuously or intermittently injecting a liquid or gas into the perforated balloon containing the hardened or partially hardened first orthopaedic paste therein until the perforated balloon is dilated to exceed a critical size, and thus ruptures.

2. The method claim 1, wherein the first bone filler comprises a hardened first orthopaedic paste as a major portion thereof, and the second bone filler comprises a hardened second orthopaedic paste as a major portion thereof, wherein the hardened first orthopaedic paste and the hardened second orthopaedic paste are both bioresorbable materials, and the hardened second orthopaedic paste has a porosity 20% higher than that of the hardened first orthopaedic paste.

3. The method claim 2, wherein the hardened second orthopaedic paste has a porosity 40% higher than that of the hardened first orthopaedic paste.

4. The method of claim 2, wherein said inserting in step ii) comprises injecting the second orthopaedic paste into the unfilled space in said bone cavity, and letting the second orthopaedic paste harden in the unfilled space.

5. The method of claim 2, wherein said inserting in step ii) comprises inserting a tube into the unfilled space in said bone cavity through a minimally invasively percutaneous path; injecting the second orthopaedic paste into the unfilled space in said bone cavity through said tube; letting the second orthopaedic paste harden in the unfilled space; and removing said tube from said percutaneous path.

6. The method of claim 2, wherein the second orthopaedic paste is calcium phosphate cement paste, calcium sulfate cement paste, or bioactive glass-based cement paste.

7. The method of claim 6, wherein the second orthopaedic paste is further doped with a bone morphogenic protein (BMP), a growth factor, or living cells for enhancing bone resorption/healing processes.

8. The method of claim 6, wherein the second orthopaedic paste is further doped with calcium phosphate particles, calcium sulfate particles, or bioactive glass particles.

9. The method of claim 2, wherein the first orthopaedic paste is calcium phosphate cement paste, calcium sulfate cement paste, or bioactive glass-based cement paste.

10. The method of claim 9, wherein the first orthopaedic paste is further doped with calcium phosphate particles, calcium sulfate particles, or bioactive glass particles for improving the compressive strength.

11. The method of claim 1, wherein the second bone filler is in granular form.

12. The method of claim 1, wherein the first bone filler and the second bone filler are both bioresorbable materials, and the second bone filler has a bioresorption rate higher than the first bone filler by at least 50%.

13. The method of claim 1, wherein a rupture array is formed on said perforated balloon for initiating said rupture of said perforated balloon when the perforated balloon is dilated to exceed said critical size.

14. The method as defined in claim 13, wherein said rupture array comprises pores, dents, notches, grooves or cuts formed on said perforated balloon, which function as weak spots so that said rupture occurs along at least a portion of said weak spots.

15. The method as defined in claim 14, wherein said weak spots form one or more dotted lines.

16. The method as defined in claim 13, wherein said rupture array is located in a region opposite to said neck of said perforated balloon.

17. The method as defined in claim 16, wherein said weak spots form one dotted line across an apex of the perforated balloon or more dotted lines intersect at an apex of the perforated balloon.

18. The method as defined in claim 13, wherein said rupture array comprises pores having a size which is penetrable to liquid contained in said orthopaedic paste but substantially impenetrable to powder contained in said orthopaedic paste under an expanded condition of said perforated balloon.

19. The method as defined in claim 18, wherein said pores constitutes a portion of said leaking perforations.

20. The method as defined in claim 18, wherein said pores constitute the whole said leaking perforations.

21. The method as defined in claim 1, wherein a forced-feeding mechanism having a liquid or gas reservoir is connected to another end of the tube, and said liquid or gas is continuously or intermittently injected from the reservoir into the perforated balloon through said tube by applying a force to said forced-feeding mechanism, until the perforated balloon is dilated to exceed said critical size.

22. The method as defined in claim 21, wherein said forced-feeding mechanism is a syringe.

* * * * *